United States Patent [19]
Webers et al.

[11] 3,994,983
[45] Nov. 30, 1976

[54] PROCESS FOR THE PRODUCTION OF LOWER ALCOHOLS BY DIRECT CATALYTIC HYDRATION LOWER OLEFINS

[75] Inventors: Werner Webers, Orsoy; Lothar Sandhack, Rheurdt; Wilhelm Neier, Orsoy, all of Germany

[73] Assignee: Deutsche Texaco Aktiengesellschaft, Germany

[22] Filed: June 12, 1975

[21] Appl. No.: 586,325

[30] Foreign Application Priority Data
June 21, 1974 Germany.............................. 2429770

[52] U.S. Cl............................... 260/641; 260/631 R
[51] Int. Cl.$^2$......................................... C07C 29/04
[58] Field of Search.................................... 260/641

[56] References Cited
UNITED STATES PATENTS

| | | |
|---|---|---|
| 2,144,750 | 1/1939 | Bent.................................... 260/641 |
| 3,548,013 | 12/1970 | Rosscup et al...................... 260/641 |

*Primary Examiner*—Joseph E. Evans
*Attorney, Agent, or Firm*—Thomas H. Whaley; Carl G. Ries; James J. O'Loughlin

[57] ABSTRACT

A process for the production of $C_2$ to $C_6$ alcohols via the direct hydration of olefins in the presence of water, and acid or a strongly acidic solid with the separation of aqueous crude alcohols from the reaction product.

18 Claims, 1 Drawing Figure

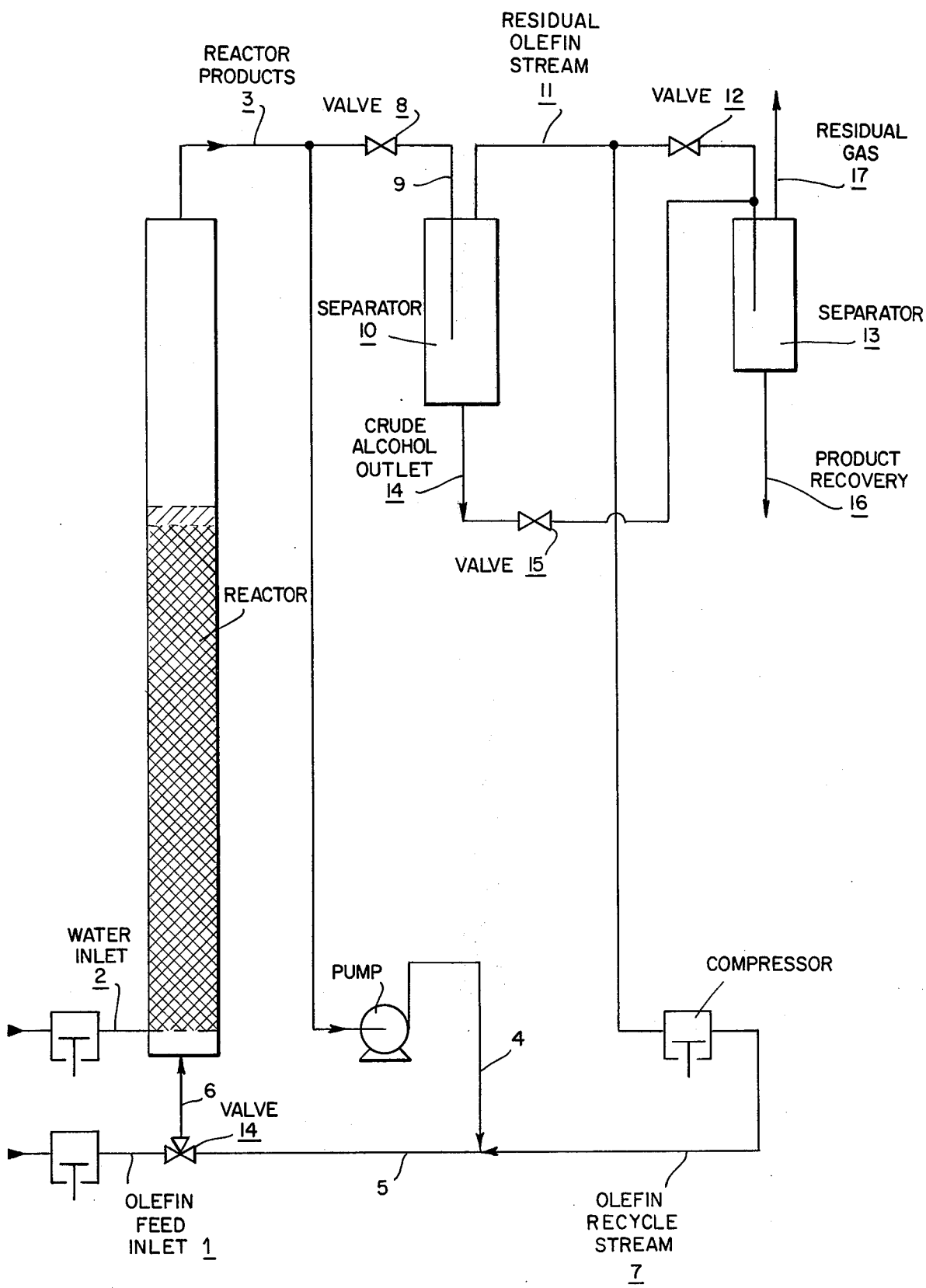

PROCESS FOR THE PRODUCTION OF LOWER ALCOHOLS BY DIRECT CATALYTIC HYDRATION LOWER OLEFINS

BACKGROUND OF THE INVENTION

1. Field of the Invention

The invention relates to the production of lower alcohols by the catalytic hydration of lower olefins in the presence of strong acids or strongly acidic solids by reacting liquid water with olefin vapour at an elevated temperature and elevated pressure with the separation of an aqueous crude alcohol from the reaction product.

2. Description Of The Prior Art

In known processes for the indirect hydration of lower olefins, such as ethylene, propylene and butylenes, for the production of lower alcohols, the olefin is initially reacted with sulphuric acid of various concentrations to produce alkyl sulphates which are eventually hydrolysed to produce the alcohols. See, for example, "Die petrolchemische Industrie" by F. Asinger (1971), Part II, pgs. 1074 – 1086 and pgs. 1098 – 1105.

In other known processes for the direct hydration of olefins, olefin and water are reacted in the vapor phase at relatively high temperatures in the presence of a catalyst consisting of solid supporting material, such as kieselguhr or the like, impregnated with orthophosphoric acid, (see, for example, U.S. Pat. No. 2,579,601, German Auslegeschriften Nos. 1,249,845 and 1,293,733 and German Offenlegungschriften Nos. 2,034,963 and 1,960,139). However, in these processes usually less than 5% of the olefin (per pass) is converted and considerable portions of the phosphoric acid catalyst are carried away in the product stream.

In other known processes, the olefin is reacted with very dilute aqueous solutions of heteropolyacids or salts thereof directly to the corresponding alcohol (see, for example German Offenlegungschrift No. 2,022,568). A similar process, which is described in German Offenlegungschrift No. 2,241,807, operates with aqueous solutions of fluorinated alkyl sulphonic acids. In accordance with German Offenlegungschrift No. 2,041,954, the catalytic action of alkyl sulphonic acid solutions or solid sulphonic acid cation exchange resins may be improved further by converting the olefin in the presence of a polyether in the liquid phase.

In various known processes, propylene or a butene is directly hydrated with liquid water in the presence of a fixed bed of an acid cation exchange resin. This reaction proceeds under temperature and pressure conditions close to or generally above the critical values of the olefins.

In several processes the reaction is carried out in continuous manner in a reactor constructed as a trickle column (see, for example, German Auslegeschrift No. 1,291,729, German Offenlegungschriften Nos. 2,147,737 to 2,147,740; 2,233,967 and 1,618,999). It is however, also known to supply the reactor packed with catalyst continuously with olefin and liquid water flowing in the upward direction and to discharge the reaction products from the top of the reactor (see German Auslegeschriften Nos. 1,105,403, and, in particular, 1,210,768) in order to improve the removal of the heat of reaction (about −10.7 to −10.9 kilocalories per mole of alcohol). However, it is evident from pages 3 and 4 of the aforementioned German Offenlegungschrift No. 1,618,999 that the results obtained by this method of operation are much inferior to those obtained by charging a trickly column at the top.

The third paragraph of column 1 and column 2 of German Auslegeschrift No. 1,136,676 describe some of the difficulties encountered when a vapor phase occurs in the charging of such reactors at the bottom. That German Auslegeschrift describes a fluidised bed system for carrying out catalytic reactions in the liquid and vapor phase.

It is an object of the invention to improve further the direct hydration of lower olefins disclosed particularly in the aforementioned German Auslegeschriften Nos. 1,105,403, 1,210,768 and 1,291,729 and German Offenlegungsschriften Nos. 2,147,737 to 2,147,740 2,233,967 and 1,618,999. These publications show that attempts have been made to improve the removal of the heat to reaction and the selectivity of the process for the formation of the alcohol by using relatively high molar ratios of water to olefin in the feed to the reactor, for example, molar ratios of water to olefin of from 10 : 1 to 20 : 1 or higher. However, this has the disadvantage that the alcohol formed is then present in the liquid reaction product in concentrations of only 8% to 12% by weight, or in even lower concentrations. For this reason, the working up of the liquid reaction product and the recovery of the alcohol therefrom by distillation have hitherto been very expensive. German Offenlegungsschrift No. 2,138,870 and German Auslegeschrift No. 1,249,844 contain proposals for facilitating the separation of the alcohol produced from the liquid reaction product, but these proposals are not generally applicable and thus have their particular disadvantages.

Furthermore, German Offenlegungsschrift No. 1,965,186 discloses a process for the production of ketones, in which the olefins are initially directly hydrated and a substantial portion of the alcohols and ether formed is simultaneously withdrawn from the hydration product by a concurrent flow, liquid phase extraction with an organic solvent. This extract, which contains a large proportion of the alcohols and ethers formed, is finally passed to a catalytic, liquid phase dehydrogenation stage to be converted into a mixture of ketones and ethers.

German Offenlegungsschrift No. 2,340,816 discloses a process for the production of sec. butanol in which liquid n-butene is continuously hydrated with water in the liquid phase in the presence of an acid cation exchange resin at a temperature of at least 100° C, and in which the molar ratio of water to olefin is maintained at above 100 : 1. However, this high molar ratio results in a very dilute aqueous solution of the alcohol the working up of which by distillation is very expensive.

Furthermore, in Example 45 of German Auslegeschrift No. 1,493,190 it is disclosed that about 700 ml of a 90% propanol may be recovered within an unspecified period of time from a mixture of 350 ml. of propanol and 350 ml. of water by passing 100 grams of ethylene through the mixture under a pressure of 200 atm. and at a temperature of 20° C. However, in the case of 50% ethanol this process has been a total failure, and in the case of 50% propanol an inadequate separating effect was obtained, since the bulk of the propanol remained in the dilute solution the concentration of which decreased only to about 45.6% when it was treated with supercritical ethylene. Only about 18% of the alcohols charged in the form of a 50% solution were obtained in a concentration of 90%.

It is an object of the invention to provide a process for the direct hydration of low olefins, in which the selectivity for the alcohol formed and its space-time yield are increased and the recovery of the alcohol from the reaction mixture is simultaneously simplified.

SUMMARY OF THE INVENTION

The invention provides a process for the production of lower aliphatic alcohols containing from 2 to 6 carbon atoms in the molecule by direct catalytic hydration of vaporous lower aliphatic olefins containing from 2 to 6 carbon atoms in the molecule, with liquid water in the presence of acids or strongly acidic solids at elevated temperature and elevated pressure with separation of an aqueous alcohols from the reaction product, which is characterized in that a. a vapor stream containing the olefin is introduced into the bottom part of a reaction vessel filled with the acid catalyst and the reaction vessel is charged with at least 1 mole of liquid water per mole of converted olefin;

b. the olefin and the water in the reaction vessel are reacted under conditions of temperature and pressure, known per se, exceeding the critical temperature and the critical pressure of the olefin charged, or at least (at the lowest) slightly below its critical temperature and pressure values;

c. either the total aqueous phase of the reaction mixture remains in the reaction vessel or the bulk thereof is returned thereto;

d. a vapor stream containing the unconverted olefin and almost the total reaction product is discharged at the top of the reaction vessel, and e. a crude liquid product consisting predominantly of the alcohol formed is separated from the vapor stream withdrawn.

In a preferred embodiment, the process according to the invention is carried out in continuous operation, at least a portion of the reaction product is removed from the vapor withdrawn from the top of the reaction vessel, the vapor is subsequently restored to the temperature and pressure conditions maintained in the reaction vessel and at least a portion thereof is introduced together with fresh olefin charge into the bottom part of the reaction vessel.

The process according to the invention is distinguished from the known direct hydration processes, in which the water component of the charge is used in the liquid state, primarily by the fact that the alcohol and ether formed are, directly after their formation, converted from the liquid phase into the vapor phase, discharged together therewith at the top of the reactor and, in the form of a liquid high-percentage crude product, are separated from the vapor phase. In the process according to the invention, the hydration of the olefin thus proceeds under known conditions of temperature and pressure above or at least (at the lowest) slightly below the temperature and pressure values critical to the olefin charged and below the decomposition temperature of any particular catalyst; however, substantially all of the alcohol and ether formed is withdrawn from the liquid reaction product with the aid of the so-called "Poynting effect" of vapors which are close to their critical point.

The process according to the invention may be carried out in various ways. The best results have been obtained by using a sump reactor (Ullmanns Encyklopaedie... 4th Ed. (1973), pages 504 et seq. Vol. 3) which is charged at the bottom with liquid water and olefin vapor and only at the top of which is withdrawn a stream of vapor containing the products.

The process according to the invention can be carried out under substantially the same conditions as those employed in the hitherto known direct hydration processes; however, in the process according to the invention it is both possible and advantageous for the molar ratio of water to olefin in the charge to be very low. A molar ratio of water to olefin considerably higher than would correspond to the ratio in the charge may, however, occur in the reactor, since only a portion of the liquid water supplied together with the charge is converted in the sump of the reactor and withdrawn together with the stream of vaporous product. Accordingly, a considerably molar excess of water (or of an aqueous acid solution) may be kept constantly available in the sump of the reactor in the process of the invention, a high selectivity of the hydration reaction for alcohol being thus ensured. It is generally sufficient for the charge to the reactor to contain about from 1 to 1.5 moles of liquid water per mole of converted olefin. Nevertheless, a molar ratio of water to olefin of from 15 to 30 or higher depending upon the required selectivity of the hydration process for the formation of alcohol may be adjusted without having to make allowance for the disadvantages involved in an elaborate recovery of the crude product from the aqueous phase. If the sump reactor is filled with a strongly acidic cation exchanger resin as catalyst, the reactor may consist of stainless steel. If, however, the reactor is constantly operated at temperature above approximately 150° C, it is favorable to protect the reactor against corrosion in a conventional manner, e.g. with titanium, silver or a polyfluorine ethylene lining. It is further possible to provide the sump reactor with an overflow to discharge excessive water or excessive liquid phase. This liquid phase discharged through the overflow may be recycled into the sump reactor at its bottom, together with the olefin charge. The recycled liquid phase may further be cooled before it is recycled into the sump reactor and partly or entirely be freed from the solved acid by means of an anion exchanger resin or the like.

However, the process according to the invention may also be carried out in a fixed bed reactor operated as a trickle column, into which the olefin is introduced at the bottom and the water at the top. Such reactor is, however, preferably filled with strongly acid ion exchange resin forming a fixed bed catalyst. But the reactor may also be packed with inert material and a recycled acid solution such as sulfuric and phosphoric acid, may be trickled on to that fixed bed. The process according to the invention may also be carried out with a bubble column reactor (Blasensaulenreaktor) filled with an aqueous acid solution through which the olefin is passed upwardly.

It has been found that far fewer byproducts are formed in the process according to the invention than in the known processes. Thus, for example, in the production of isopropanol described in German Auslegeschrift No. 2,147,740 (for instance in Examples 10 and 11), the proportion of di-iso-propyl ether in the crude product amounted to about 3 to 4 wt. % based on the organic material, when the reactor was charged with 800 grams (44.44 moles) of water and 123 grams (2.69 moles) of a 92% propylene per litre of catalyst per hour in downwardly directly concurrent flow at a temperature in the range 135°–155° C and a pressure of about 100 atmospheres gauge. The molar ratio of water to olefin was thus about 15 : 1, and 200 grams (11.11 moles) of additional water per litre of catalyst per hour were introduced separately. About 75% of the propylene charged was converted, about 2 moles of isopropanol per litre of catalyst per hour being obtained. In comparison therewith, as the Examples given hereinafter will show, the throughput, that is to say the space velocity of the olefin charged in the process according to the invention, may be considerably increased, the space-time yield of alcohol may be increased simultaneously and the reaction may be carried out with a charge in which the water and the olefin are present in a molar ratio of about 1.5 : 1 and a selectivity of 99% or higher for alcohol may be obtained. The high selectivity of the process according to the invention is attributed to the fact that the concentration of alcohol in the liquid phase is maintained at an extremely low value. The increased performance of the same catalyst is attributed to the fact that the reaction equilibrium is continuously shifted in the direction of the products as a result of the substantially direct conveying of the products into the vapor phase.

It has also been found that the difficulties arising in the known direct hydration processes in connection with the removal of the reaction heat and maintaining as an uniform as possible distribution of the temperature in the fixed bed catalyst do not arise when the molar ratio of water to olefin in the charge is reduced from the conventional value of 15 – 20 : 1 or higher to a ratio of 1.5 – 2 : 1, and the throughput and conversion of the olefins are further increased.

In the process according to the invention, the heat of hydration is removed as a result of the conveying of the alcohol formed into the vapor phase and also as a result of the high specific heat of the vapor phase which is supercritical or close to its critical point.

A gas or vapor stream consisting at least predominantly of the actual olefin to be converted serves advantageously as the vapor phase by which the product is extracted or removed. However, the process according to the invention may also be operated with a gas or vapor stream which does not participate in the hydration reaction, provided its critical values are close to or slightly below the conditions of temperature and pressure under which the reaction is carried out. The last mentioned method does, however, result in a reduced space-time yield.

This vapor stream which, for the sake of simplicity, is referred to as a "supercritical vapor phase" is advantageously recycled (upwardly) through the fixed bed reactor and the reaction product is separated from the recycled vapor stream leaving the reactor (at the top) by partial expansion and, if necessary, additional cooling, in liquid form. Since, as in the known trickle process, the process according to the invention results in a high degree of conversion of the olefin, after separation of the product from the supercritical vapor phase, the return of the latter to the reactor may be dispensed with and it may be passed to other suitable use.

The process according to the invention as applied to the production of isopropanol (IPA) from propylene and of sec. butanol (SBA) from butylene e.g. butene-1, and butene-2 in the presence of an acid cation exchange resin as fixed bed catalyst is illustrated in detail in the following Examples. The process according to the invention is, however, not limited to these catalysts or to these starting materials; it may also be applied to the hydration of ethylene, isobutylene, n-pentene, 2-pentene, 1-hexene, 2-hexene, cyclohexene and the like to the corresponding alcohols the hydration of $C_3$ and n-$C_4$ olefins being, however, preferred.

The Examples are described with reference to the accompanying drawing which shows a flow diagram of one embodiment of the process according to the invention.

EXAMPLE 1

A vertical reaction tube made of stainless steel and having an internal diameter of 26 mm. and a length of 3 metres, was filled with 1.5 litres of Raschig rings (stainless steel, 4 × 4 mm) up to a level of 2.83 m and then, up to the same level, with 1.2 litres of a commercially available macroporous cation exchange resin (sulphonated styrenedivinyl benzene copolymer) in H form. The fixed bed comprising packing and catalyst so obtained was held in position by stainless steel wire netting disposed below it and above it.

245 grams per hour of a $C_3$-gas mixture containing 96% (5.6 moles/hour) of propylene were introduced into the bottom of the reaction tube through a conduit 1 and water was introduced at a rate of 139 grams (7.7 moles) per hour into the bottom of the reactor through a conduit 2. A temperature of 135° C and a pressure of 100 atmospheres gauge were maintained in the reactor.

The vaporous reaction product was withdrawn from the gas space at the top of the reactor through a conduit 3. A portion of the reaction product was recycled by a circulation pump through conduits 4, 5 and 6 to the reactor and was simultaneously mixed with residual gas recycled through conduit 7, and the fresh gas stream admitted through conduit 1 to produce a gaseous mixture containing about 86% – 91% of propylene, which mixture was introduced into the reactor.

A valve 8 was provided in conduit 3 at a position downstream of the branch extending to the pump, the valve serving to reduce the pressure on the remaining partial stream of reaction product to 25 – 30 atmospheres gauge, that partial stream being then introduced into a first separator 10. A liquid crude alcohol was obtained in the first separator 10 after separation of a residual $C_3$ gas, and the liquid alcohol was allowed to expand through conduit 14 and valve 15 into a second separator 13.

The residual gas containing 85.4% of propylene was passed from the first separator 10 through a conduit 11 to a compressor to be compressed to a pressure of 100 atmospheres gauge and from which it was returned to the reactor through conduit 7, conduit 5, a valve 14 and conduit 6, that is to say together with the recycled stream from conduit 4 and the 96% fresh gas stream from conduit 1 in the form of a gaseous mixture containing from 96% to 91% of propylene.

An amount of residual gas which contained 58.8 grams (1.4 moles) of propylene and 10 grams (0.227 mole) of propane, was withdrawn per hour from the cycle through a valve 12 which was connected to conduit 11. The pressure of the residual gas was reduced to atmospheric in a second separator 13 and that residual gas was then fed to a reconcentration unit (not shown). 252 grams (4.2 moles) of isopropanol, 0.5 grams (0.005 mole) of di-isopropyl ether and 63 grams (3.5 moles) of water per hour were obtained in the separator 13 after removal of the $C_3$ constituent in the form of an 80% alcohol.

The space-time yield of IPA amounted to 3.5 moles per litre of catalyst per hour, and the IPA selectivity exceeded 99%.

EXAMPLE 2

The process described in Example 1 was repeated except that 232 grams per hour of an 87% n-butene mixture (3.6 moles) were introduced through conduit 1 and 58 grams (3.2 moles) of water per hour were fed through conduit 2 into the reactor in which a temperature of 150° C. and a pressure of 70 atmospheres gauge were maintained. The butene concentration in the mixture comprising fresh gas, recycle butene and the butene present in the residual gas, returned through conduit 6 was adjusted to 76–81%.

When the $C_4$ hydrocarbons, which were gaseous under normal conditions, had been removed, the crude alcohol obtained in the separator 13 comprised 89% secondary butyl alcohol (SBA), from 0.5 to 1.0% of di-sec. butyl ether and about 10% of water. A total of 117 grams (1.6 moles) of SBA per litre of catalyst per hour were obtained. The selectivity for SBA was about 99%.

As can be seen from the foregoing examples, the selectivity of the reaction with propylene and n-butene were both 99 percent and the alcohol yields of isopropyl alcohol and secondary butanol were 80 percent and 89 percent respectively. These results represent substantial and surprising improvements in the continuous catalytic direct hydration of aliphatic olefins to the corresponding aliphatic alcohols.

We claim:

1. A continuous process for the production of isopropyl alcohol by the direct catalytic hydration of propylene with water, the improvement which comprises; conducting said reaction in a reactor divided into an upper and lower zones, said lower zone being filled with liquid water and containing an insoluble olefin hydration catalyst therein to form a liquid phase reaction zone, and said upper zone being a vapor phase zone, introducing propylene charge into the bottom of said liquid phase reaction zone, continuously introducing feed water into said liquid phase reaction zone in a ratio of from 1 to 3 moles of feed water per mole of converted propylene, maintaining catalytic hydration conditions in said reactor including an amount of water in said liquid phase reaction zone ranging from 15 to 30 moles of water per mole of propylene being reacted, continuously withdrawing a vaporous product stream from said vapor phase zone of said reactor comprising isopropyl alcohol, unreacted propylene and steam, partially condensing said vaporous product stream to liquify said isopropyl alcohol and steam to form a crude liquid fraction and leave a vaporous fraction containing unreacted propylene, recycling said vaporous fraction containing unreacted propylene to the bottom of said liquid phase reaction zone, and recovering isopropyl alcohol from said crude liquid fraction.

2. A process according to claim 1, in which the molar ratio of feed water to converted propylene ranges from 1:1 to 1.5:1.

3. A process according to claim 1, in which said hydration catalyst is a strongly acidic cation exchange resin catalyst.

4. A process according to claim 1, in which said reactor is maintained at a temperature ranging from about 135°–155° C under a pressure ranging from 50 to 150 atmospheres.

5. A process according to claim 1, in which said propylene charge is a $C_3$ hydrocarbon mixture containing at least about 70% by volume of propylene.

6. A process according to claim 1, in which said vaporous product stream from said reaction on a propylene-free basis comprises about 80% by weight of isopropyl alcohol, about 0.2% by weight of diisopropyl ether and the balance steam.

7. A process according to claim 1, in which said reactor is a sump reactor.

8. A process according to claim 1, in which said propylene charge consists of at least 86 percent propylene.

9. A process according to claim 1, in which an inert sweep gas is charged into the bottom of said liquid phase reaction zone.

10. A process according to claim 1, in which said reactor is a fixed-bed reactor.

11. A process according to claim 1, in which said olefin hydration catalyst is a sulfonated styrenedivinyl benzene copolymer in the acid form.

12. A continuous process for the production of secondary butyl alcohol by the direct catalytic hydration of n-butene with water, the improvement which comprises conducting said reaction in a reactor divided into an upper and lower zones, said lower zone being filled with liquid water and containing an insoluble olefin hydration catalyst therein to form a liquid phase reaction zone, and said upper zone being a vapor phase zone, introducing an n-butene charge into the bottom of said liquid phase reaction zone, continuously introducing feed water into said liquid phase reaction zone in a ratio of from 1 to 3 moles of feed water per mole of converted n-butene, maintaining catalytic hydration conditions in said reactor including an amount of water in said liquid phase reaction zone ranging from 15 to 30 moles of water per mole of said n-butene being reacted, continuously withdrawing a vaporous product stream from said vapor phase zone comprising secondary butyl alcohol, unreacted n-butene and steam, partially condensing said vaporous product stream to liquify said secondary butyl alcohol and steam to form a crude liquid fraction and leave a vaporous fraction containing unreacted n-butene, recycling said vaporous fraction containing unreacted n-butene to the bottom of said liquid phase reaction zone and recovering secondary butyl alcohol from said crude liquid fraction.

13. A process according to claim 12, in which the molar ratio of said feed water to said n-butene ranges from 1:1 to 1.5:1.

14. A process according to claim 12, in which said hydration catalyst is a strongly acidic cation exchange resin catalyst.

15. A process according to claim 12, in which said reactor is maintain at a temperature ranging from 120 to 180° C, under a pressure ranging from about 50 to 150 atmospheres.

16. A process according to claim 12, in which the vaporous product stream from said reaction on an n-butene-free basis comprises about 89 percent secondary butyl alcohol, from 0.5 to 1 percent of di-secondary butyl ether and about 10 percent steam.

17. A process according to claim 12, in which said reactor is a sump reactor.

18. A continuous process for the production of an aliphatic alcohol having from 2 to 6 carbon atoms by the direct catalytic hydration of a monoolefin having from 2 to 6 carbon atoms with water, the improvement which comprises conducting said reaction in a reactor divided into an upper and lower zones, said lower zone being filled with liquid water and containing an insoluble olefin hydration catalyst therein to form a liquid phase reaction zone, and said upper zone being a vapor phase zone, introducing a monoolefin having from 2 to 6 carbon atoms into the bottom of said liquid phase reaction zone, continuously introducing feed water into said liquid phase reaction zone in a ratio of from 1 to 3 moles of feed water per mole of converted monoolefin, maintaining catalytic hydration conditions in said reactor including an amount of water in said liquid phase reaction zone ranging from 15 to 30 moles of water per mole of said monoolefin being reacted, continuously withdrawing a vaporous product stream from said vapor phase zone comprising an aliphatic alcohol having from 2 to 6 carbon atoms, unreacted monoolefin having from 2 to 6 carbon atoms and steam, partially condensing said vaporous product stream to liquify said alcohol and steam to form a crude liquid fraction and leave a vaporous fraction containing unreacted monoolefin, recycling said vaporous fraction containing unreacted monoolefin to the bottom of said liquid phase reaction zone and recovering an aliphatic alcohol from said crude liquid fraction.

\* \* \* \* \*